(12) United States Patent
Misner et al.

(10) Patent No.: US 6,222,189 B1
(45) Date of Patent: Apr. 24, 2001

(54) METHODS OF ENHANCING OPTICAL SIGNALS BY MECHANICAL MANIPULATION IN NON-INVASIVE TESTING

(75) Inventors: Michael Misner, San Diego, CA (US); Howard E. Guthermann, Newton, MA (US); Myron J. Block, Jupiter Island, FL (US)

(73) Assignee: Optix, LP, Jupiter Island, FL (US)

( * ) Notice: Subject to any disclaimer, the term of this patent is extended or adjusted under 35 U.S.C. 154(b) by 0 days.

(21) Appl. No.: 09/073,575

(22) Filed: May 6, 1998

Related U.S. Application Data

(60) Continuation-in-part of application No. 08/937,934, filed on Sep. 25, 1992, now Pat. No. 6,064,065, which is a division of application No. 08/479,955, filed on Jun. 7, 1995, now Pat. No. 5,672,875, which is a continuation-in-part of application No. 08/333,758, filed on Nov. 3, 1994, now Pat. No. 5,818,048, which is a continuation-in-part of application No. 08/182,572, filed on Jan. 14, 1994, now Pat. No. 5,424,545, which is a continuation-in-part of application No. 08/130,257, filed on Oct. 1, 1993, now Pat. No. 5,434,412, which is a continuation-in-part of application No. 07/914,265, filed on Jul. 15, 1992, now Pat. No. 5,321,265.

(51) Int. Cl.$^7$ .................................................. G01N 21/25
(52) U.S. Cl. ..................... 250/341.1; 600/335; 356/39
(58) Field of Search .......................... 290/341.1, 341.5, 290/339.12; 356/39, 40, 42; 600/322, 331, 335

(56) References Cited

U.S. PATENT DOCUMENTS

| | | |
|---|---|---|
| 2,706,927 | 4/1955 | Wood . |
| 4,167,331 | 9/1979 | Nielsen ................................. 356/39 |
| 4,222,389 | 9/1980 | Rubens ................................. 128/633 |
| 4,266,554 | 5/1981 | Hamaguri ............................. 128/633 |
| 4,463,762 | 8/1984 | Rubens ................................. 128/633 |
| 4,883,953 | 11/1989 | Koashi et al. ....................... 250/226 |
| 4,927,264 | 5/1990 | Shiga et al. ........................... 356/41 |
| 4,984,577 | 1/1991 | Frankenreiter ....................... 128/681 |
| 5,178,142 | 1/1993 | Harjumnaa et al. ................. 128/633 |
| 5,183,042 | 2/1993 | Harjumnaa et al. ................. 128/633 |
| 5,321,265 | 6/1994 | Block ................................... 250/393 |
| 5,372,135 | 12/1994 | Mendelson et al. ................. 128/633 |

(List continued on next page.)

OTHER PUBLICATIONS

Robert D. Boehmer, PhD , Continuous, Real–Time, Noninvasive Monitor of Blood Pressure: Penaz Methodology Applied to the Finger, Journal of Clinical Monitoring 1987 282–287.

(List continued on next page.)

*Primary Examiner*—Seungsook Ham
*Assistant Examiner*—Richard Hanig
(74) *Attorney, Agent, or Firm*—Lahive & Cockfield, LLP

(57) ABSTRACT

The invention relates to the enhancement of the signal-to-background ratio of a non-invasive measurement of the concentration of a blood constituent at a measurement site by applying an external pressure at a location near the measurement site. In one embodiment, sufficient pressure is applied proximate to a measurement site to stop blood flow. The pressure is then suddenly relased, thereby generating a blood bolus passing through the site. By illuminating the measurement site before and during the passage of the blood bolus and observing the interaction of the input radiation with the measurement site, the concentration of a blood constituent can be measured. In another embodiment, the venous pulse is occluded by applying a pressure midway between systolic and diastolic pressure. By illuminating the measurement site in the absence of a venous pulse, the signal-to-background ration can be enhanced and the concentration of a blood constituent can be measured.

18 Claims, 3 Drawing Sheets

U.S. PATENT DOCUMENTS

| | | | |
|---|---|---|---|
| 5,372,136 | 12/1994 | Steuer et al. | 128/633 |
| 5,434,412 | 7/1995 | Sodickson et al. | 250/343 |
| 5,459,317 | 10/1995 | Small et al. | 250/341.1 |
| 5,499,627 | 3/1996 | Steuer et al. | 128/633 |
| 5,596,986 * | 1/1997 | Goldfarb | 600/323 |
| 5,638,816 | 6/1997 | Kiani-Azarbayjany et al. | 128/633 |

OTHER PUBLICATIONS

Y. Nomura, O. Hazeki, and M. Tamura, *Exponential Attenuation of Light along Nonlinear Path through the Biological Model*, 77–80 (printed in Japan).

Motoki Oda et al., A Simple and novel algorithm for time–resolved multiwavelenght oximetry, Phys. Med. Biol. 41 (1996) 551–562. (printed in the UK).

* cited by examiner

METHODS OF ENHANCING OPTICAL SIGNALS BY MECHANICAL MANIPULATION IN NON-INVASIVE TESTING

REFERENCE TO RELATED APPLICATIONS

The present application is a continuation-in-part of U.S. patent application Ser. No. 08/937,934, filed Sep. 25, 1997, now U.S. Pat. No. 6,064,065 entitled METHODS OF MINIMIZING SCATTERING AND IMPROVING TISSUE SAMPLING IN NON-INVASIVE TESTING AND IMAGING, which is a divisional of U.S. patent application Ser. No. 08/479,955, filed on Jun. 7, 1995, entitled METHODS OF MINIMIZING SCATTERING AND IMPROVING TISSUE SAMPLING IN NON-INVASIVE TESTING AND IMAGING, now United States Patent No. 5,672,875, which is a continuation-in-part of U.S. patent application Ser. No. 08/333,758, entitled RAPID NON-INVASIVE OPTICAL ANALYSIS USING BROAD BANDPASS SPECTRAL PROCESSING, filed Nov. 3, 1994, now U.S. Pat. No. 5,818,048, which is itself a continuation-in-part of U.S. patent application Ser. No. 08/182,572, entitled NON-INVASIVE NON-SPECTROPHOTOMETRIC INFRARED MEASUREMENT OF BLOOD ANALYTE CONCENTRATIONS filed Jan. 14, 1994, now U.S. Pat. No. 5,424,545, which is a continuation-in-part of U.S. patent application Ser. No. 08/130,257, entitled IMPROVEMENTS IN NON-SPECTROPHOTOMETRIC MEASUREMENT OF ANALYTE CONCENTRATIONS AND OPTICAL PROPERTIES OF OBJECTS, filed Oct. 1, 1993, now U.S. Pat. No. 5,434,412, which is a continuation-in-part of U.S. patent application Ser. No. 07/914,265, entitled NON-INVASIVE TESTING, filed Jul. 15, 1992, now U.S. Pat. No. 5,321,265. Disclosures of all the preceding applications are incorporated herein by reference.

BACKGROUND OF THE INVENTION

The present invention relates to the use of radiation, preferably near-infrared radiation to detect and measure the concentration of constituents or other properties of interest of a material. More particularly, apparatus and methods have been developed for measurement of the concentration of constituents such as hemoglobin and its variants and derivatives, glucose, cholesterol and its combined forms, drugs of abuse, and other analytes of clinical and diagnostic significance in a non-invasive manner.

Because the apparatus developed for use of this method does not require the withdrawal of blood in order to perform these measurements, it is particularly suitable for testing in the home on a chronic basis such as for glucose levels in diabetics and for kidney function, e.g., urea or creatinine testing, in patients undergoing home dialysis. The present invention uses a variety of methods to change the pathlength through tissue and/or the blood volume within an optically sampled tissue to help distinguish the desired signal produced by one or more components of the blood volume from background noise produced by tissue or other components of the blood volume and from the background noise of the system itself.

The development of clinical testing procedures that do not require the withdrawal of blood has become an important goal due to the spread of AIDS and the associated fears among the public and health care personnel. Along with AIDS, other diseases, such as hepatitis, can be spread through the use of invasive procedures without stringent precautions to assure sterility. "Nosocomial transmission of hepatitis B virus associated with the use of a spring-loaded finger-stick device," *New England Journal of Medicine.* 326(1 1), 721–725 (1992), disclosed a hepatitis mini-epidemic in a hospital caused by the improper use of an instrument for obtaining blood samples. The article describes how the hospital personnel unintentionally transmitted the virus from patient to patient by misuse of the sampling device. Such transfers, potentially hazardous to health care personnel as well as to patients, are eliminated by the non-invasive testing method performed by the apparatus and method of the invention.

Non-invasive testing will become particularly effective in the long-term management of diabetes. Improperly controlled glucose levels in diabetics can result in damage to the circulatory system, the nervous system, the retina and other organs. This damage can be largely eliminated by more effective control of glucose levels. However, this level of control requires the measurement of glucose levels four or more times a day. With current apparatus and methods, a painful finger prick is required for each such measurement. Furthermore, that part of the apparatus that contacts the blood to produce the required chemical change used in the measurement is disposed of after each measurement. The cost of these disposables can run thousands of dollars per year. The inconvenience and discomfort of glucose measurement exacts a further psychological toll from the diabetic. Finally, because the sampling process is conducted by relatively untrained personnel, it is prone to error. These errors have been reported to be as high as three to five times the inherent error in the process. Errors in the sampling process can occur either as a result of failure to obtain a proper blood sample (e.g., the sample may be an admixture of intracellular or interstitial fluid or blood) or failure to correctly apply the sample to the disposable part of the apparatus, or both.

These deficiencies in currently available apparatus and methods have caused a number of groups to attempt to develop devices for non-invasively measuring concentrations of various blood constituents. The most commercially successful devices for the non-invasive measurement of chemical constituents of blood are those that use "pulse oximetry" to measure the relative concentrations of oxyhemoglobin and deoxyhemoglobin. Because these two constituents are both highly absorptive in the near infrared and because of their crossing broadband features, the ratio of radiation intensities at two wavelengths can provide the requisite information. Based in part on the success of hemoglobin ratio measurements, much current work on non-invasive concentration measurements for chemical constituents of blood has also used the near-infrared region of the electromagnetic spectrum. Because of the number of diabetics most of this research is directed to techniques for the non-invasive measurement of blood glucose levels. Although glucose is present in low concentration, and although glucose has low absorptivity, the wavelength band between 700 nm and 1100 nm contains the third overtones of the glucose absorption spectrum. This band theoretically allows minimization of interference due to water absorption and exhibits good penetration of human tissue. Other promising research has used longer wavelengths, from 1100 nm to about 2500 nm.

Substantially all of this work has been carried out using variants on classic spectrophotometric methods. Classical methods typically use detectors which measure the radiation transmitted through or reflected from the sample in a relatively narrow wavelength passband. The passband is kept narrow for several reasons. First, a narrow passband reduces the practical deviations that can occur relative to the theoretical relationships between constituent concentration and absorbance. Second, a narrow detector passband allows better measurement of sharply peaked spectra by providing a measurement closer to the spectral peak of the constituent of interest. According to classical methods, this improves specificity, and for full-spectrum measurements, provides a more faithful rendition of the absorbance or reflectance spectrum.

The wavelength passband within which the detector operates can either be a property of the source or can be obtained by placement of an appropriate filter between the source and the sample, between the sample and the detector, or both. The width of the passband in classic spectrophotometry is ordinarily chosen to be small relative to the width of the spectral features of the constituent of interest and of the sample. Typically, a passband half-width of less than 10% of the spectral half-width is recommended.

In some spectrophotometric devices, the source is designed to scan the spectral region of interest so that the measured wavelength varies with time in a controlled manner. In other cases, the source is transformed into a coded broadband source whose interaction with the sample is later decomposed into narrow-band responses.

In most classic spectrophotometric devices and methods, the measured data is initially in the form of an uncorrected intensity versus wavelength. The next important step, performed within the spectrophotometric apparatus, is a logarithmic conversion of the data into absorbance or reflectance units using some reference intensity versus wavelength data for normalization. Extensive data processing of the transformed data is then employed in an attempt to isolate the components of the data arising from the constituent(s) of interest from the components arising from the background (due to constituents that are not of interest and instrumental artifacts). Many techniques are available for this isolation, virtually all of which are based on statistical regression techniques. Examples of this general approach include the works of Rosenthal, U.S. Pat. No. 5,023,737, and of Clarke, U.S. Pat. No. 5,054,487.

All of these classical spectrophotometric methods essentially search for a unique response or pattern of responses due to the constituent of interest at one or more specific wavelengths (or narrow wavelength passbands) and then attempt to separate these effects from the effects due to background constituents at those same narrow wavelength passbands. However, glucose and many other constituents of interest possess only weak broadband spectral features in the wavelength ranges of interest. Furthermore, the measurement environment is generally a mixture containing glucose and many other constituents having overlapping but different broadband spectral structures several of which, including water and the hemoglobin species, are strong absorbers in the wavelength ranges of interest. In non-invasive clinical measurements, these problems are further compounded by the presence of multiple diffuse radiation scattering centers in the tissue. As a result, the overall measurement environment is not conducive to the use of classical spectrophotometric techniques.

U.S. Pat. No. 5,321,265 (the "Block '265 patent") discloses a system having a plurality of filters with overlapping passbands analogous to the overlapping passbands of the human eye's photoreceptors. The disclosed methods and devices use a broadband radiation source to illuminate a sample held in a chamber. Radiation from the broadband source is passed through a plurality of spectrally overlapping filters before reaching the detectors. These detectors detect the radiation transmitted, reflected or emitted from the sample and thereby measure the sample's "color" in the region of the spectrum defined by the filter and detector responses. U.S. Pat. No. 5,434,412 (the "Sodickson '412 Patent") and U.S. Pat. No. 5,424,545 (the "Block '545 Patent") concern modifications to the basic devices and methods disclosed in Block '265 to achieve better results.

The present invention concerns additional methods and devices which may be employed toward the measurement of a sample's color in pulse oximetry, and in standard photometric and spectrophotometric measurements for in vivo systems. The methods and devices of the invention are all directed to the use of mechanical stimuli for improving the accuracy, sensitivity, and repeatability of non-invasive measurements of blood constituents such as glucose. This is achieved in the invention by the use of mechanical stimuli to increase the optical magnitude of normal cardiac pulses, to generate a change in volume either within the blood or within the extra-cellular and intra-cellular compartments of the tissue, or to provide an estimate of tissue scattering.

The use of mechanical stimuli to enhance the signal-to-background ratio in pulse oximetry is well known. First, the measurement of the pulsatile portion of the data segregates the response of the blood from the interfering background response of the tissue lying in the optical path. Second, since only the arterial component of blood volume changes with each pulse, pulsatile measurement further segregates the arterial blood response from the venous blood response. This is particularly significant in pulse oximetry since arterial blood is considerably more saturated with oxygen than venous blood.

The use of mechanical stimuli, in the form of direct pressure, has long been considered essential in the non-invasive measurement of blood pressure. Its use in pulse oximetry applications has been considered for a number of years. For example, Wood (see U.S. Pat. No. 2,706,927) suggests that signal characteristics might be improved by squeezing the earlobe to remove the blood and then restoring blood flow after the measurement. Similarly, Shiga and Suzaki (U.S. Pat. No. 4,927,264) suggest using a pressure of approximately diastolic pressure in pulse oximetry. Both groups however, used the pressure for measurement of hemoglobin ratios in venous blood only. In fact, Shiga et al. specifically made their arterial measurements without applied pressure. Many of the pulse oximetry instruments on the market (for example, Nellcor, Pleasanton, Calif.; Novametrix, Wallingford, Conn.) maintain mild, steady pressure on the skin near the measurement site. However, there is no active use of the applied pressure in generating improved data.

In other disclosures, Harjunmaa et al. see U.S. Pat. Nos. 5,178,142 and 5,183,042 and Mendelson et al. see U.S. Pat. No. 5,372,135 demonstrate the possibility of compressing tissue to either change the volume of venous blood in the tissue or to change the ratio of intracellular to extracellular fluid volume. However, none of these disclosures demonstrate active control over the cardiac pulse to generate a change in arterial blood volume with improved properties for use in generating improved photometric data, nor do they indicate the possibility of creating controllable pulsatile variations in tissue optical characteristics to improve the measurement of such characteristics. Finally, Kiani-Azarbayjany et al. (U.S. Pat. No. (5,638,816) discloses that a pressure-induced pulse, separate from that of the cardiac cycle, may be used to alter blood volume and thereby increase signal-to-background ratio. However, this disclosure does not disclose methods of applying constant pressure for amplifying the normal cardiac pulse, nor does it reveal the superior methods disclosed herein for inducing the non-cardiac pulse.

For in vivo measurement of materials which have a much lower concentration or which provide a much lower signal, such as glucose, the natural pulsatile modulation, which is much lower in amplitude than the total signal, may be so small as to be useless. This is particularly likely for classical spectrophotometric measurements which have very low signal-to-background ratios when the concentration of the constituent of interest is low.

Accordingly, an object of the invention is to provide methods of using controlled mechanical stimuli to improve the signal-to-background ratio of in vivo non-invasive optical measurement devices.

A further object of the invention is to utilize controlled mechanical stimuli to improve methods for measuring the concentrations of constituents in arterial blood non-invasively.

A still further object of the invention is to generate improved artificial pulses to obtain greater sensitivity in non-invasive optical measurements.

Another object of the invention is to provide a measure of tissue scattering at a measurement site.

These and other objects and features of the invention are achieved by the methods and apparatus described in the Summary of the Invention, the Detailed Description and the Drawing.

SUMMARY OF THE INVENTION

The subject invention relates to various methods by which variations of the optical properties of tissue can be controllably introduced or enhanced in order to provide an increased signal-to-background ratio for non-invasive measurements. The methods disclosed in the subject invention employ varying amounts, locations of application, and frequencies of application of various stimuli to the circulatory system and/or to the tissue of the body. Different, controllable responses to the stimuli from the circulatory system or from the tissue may be obtained. These responses, in turn, produce controllable variations in the pathlengths of optically active compartments within the tissue. The controllable variations in pathlength thereby produce controllable variations in optical responses to radiation traveling through the tissue, as measured by appropriately configured detectors, in such a manner as to provide detector signals with increased signal-to-background ratios upon proper processing of these signals. These methods use a variety of mechanical stimuli to achieve this improved ratio.

In all the embodiments, the measurement site is illuminated by the selected radiation. This radiation can be either transmitted through, reflected from, or transflected from the measurement site. The detected signal is then analyzed, using methods known in the art, to determine the concentration of the constituent of interest.

In one method embodying the invention, a constant mechanical pressure is applied in an amount between diastolic and systolic pressure, thereby enhancing the mechanical pulsatility of the arterial wall by reducing wall stress, while still allowing arterial flow. A site adjacent to the measurement site is optimal for application of this mechanical pressure. The application of said mechanical pressure substantially enhances the pulse relative to the magnitude of the normal cardiac pulse, thereby improving signal-to-background ratios.

In another embodiment of the invention, the applied mechanical pressure exceeds the systolic pressure generated by the heart. While said mechanical pressure is maintained, arterial and venous blood flow are both halted. The relaxation of the mechanical pressure distal to the site of the application of the mechanical pressure empties the arterial volume into the venous volume of the body part. This redistribution of blood away from the optical path causes an increase in transmission of the radiation through the measurement site. Then, upon removal of the applied mechanical pressure, the inrush of blood (called a blood bolus) into the body part and subsequent redistribution of the blood volume causes a reduction in transmission. These induced transmission pulses are significantly larger than those caused by the natural cardiac pulse or the enhanced cardiac pulse.

In yet another embodiment, mechanical forces are applied by altering the hydraulic pressure existing between the heart and the measurement site. Such an alteration will change the venous blood volume at that site. One easy way to provide this alteration is to move an extremity, such as an arm, so that it is above or below the heart. Measurement of radiation passing through the site before and after such a change thereby provides information segregating the venous optical absorption from that of the tissue.

In another embodiment, the application of a mechanical force is undertaken at the measurement site itself to compress the tissue, thereby driving some of the water from the site and modifying the pathlength at the site. This applied pressure can be used to standardize the sample, thereby eliminating a variable in the processing of data.

These and other embodiments are further elaborated in the Detailed Description and in the claims.

BRIEF DESCRIPTION OF THE DRAWINGS

FIG. 1B shows a photometric transmission measurement of the arterial pulse of FIG. 1A; and.

DETAILED DESCRIPTION OF THE INVENTION

The present invention relates to methods of enhancing signal-to-background in non-invasive measurements of blood components. These methods are primarily focused on the application of a mechanical pressure or force at or near the measurement site. The application of the mechanical pressure changes the blood volume and/or the pathlegnth of measurement to increase the signal obtained from the interaction of incident radiation with the bold component of interest, or decrease the background which interferes with the measurement.

Figure 1A:
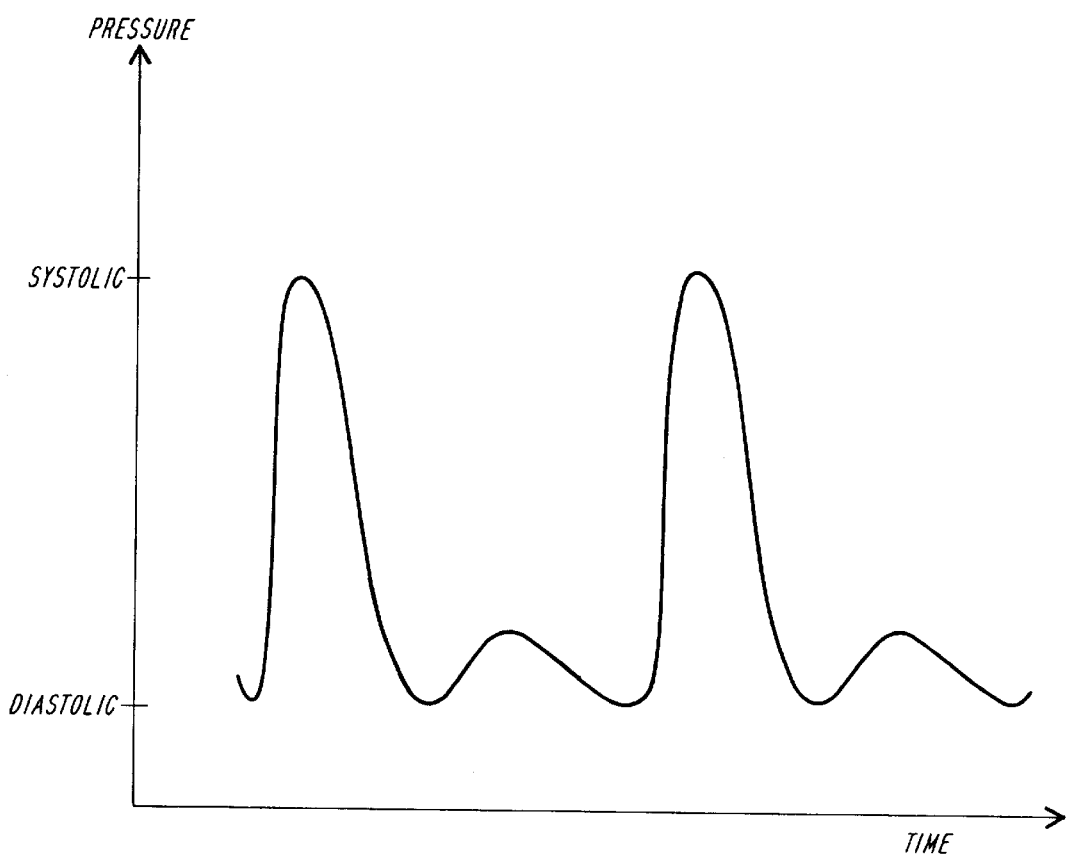
FIG. 1A illustrates the normal arterial pulse, measured by a blood pressure measurement.

The arterial pressure pulse created by the beating of the heart in normal human subjects is illustrated in FIG. 1A. The magnitude of the peak and the shape of the curve at a particular measurement site are both complex functions of the pumping action of the heart, the physical properties of the blood (such as density and viscosity), the physical dimensions and properties of the blood vessels, both proximal and distal to the measurement site, the physical dimensions and properties of the tissue surrounding the arterial blood vessel in which the pulse is being measured, and the location and method used to measure the pressure.

Figure 1B:
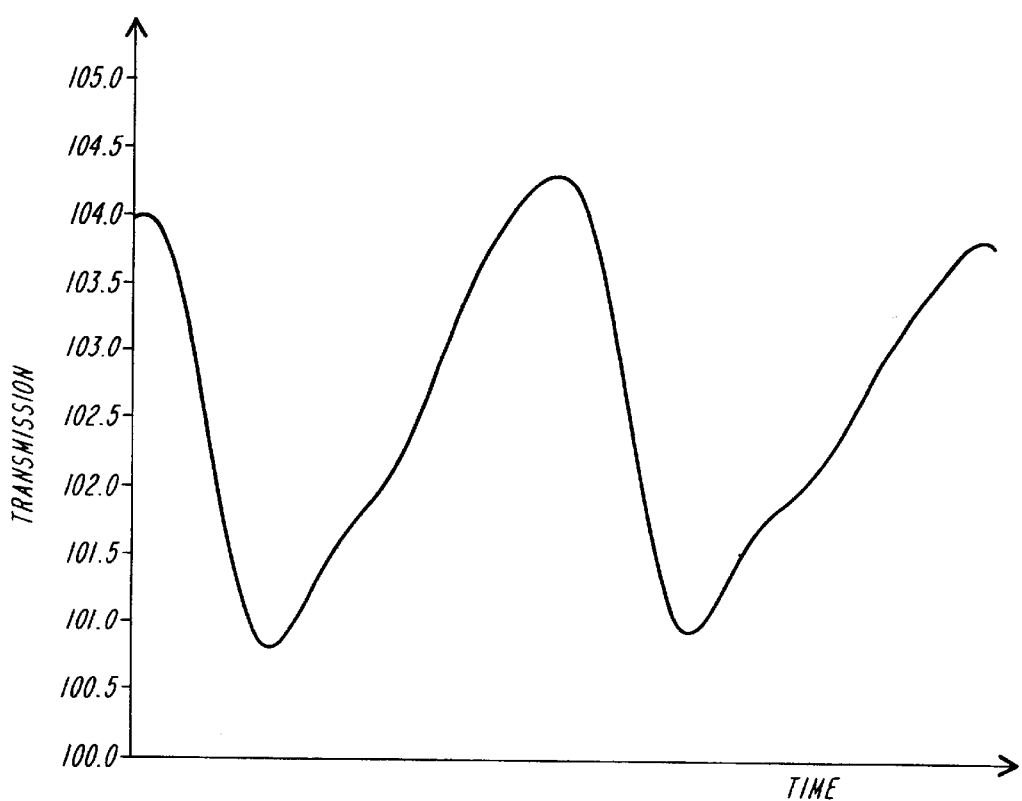

FIG. 1B, on the same time scale as FIG. 1A, shows the intensity of radiation transmitted through a tissue volume having one or more arterial vessels contained within it. For the purposes of this graph, the illuminating radiation is assumed to include those wavelengths in which the hemoglobin species are the dominant absorbers (i.e., 700–1200 nm) and the detector whose response is graphed is assumed to be responsive to radiation in that same region of the spectrum. It is generally believed that the similarity between the waveform of FIG. 1B and the pressure waveform of FIG. 1A occurs because the modulation (decrease) in transmission arises from an increase in the optical pathlength through the arterial vessels produced by their expansion during the systolic phase of the pressure waveform. One basis for this assumption is that non-invasive pulse oximetry measurements based on this assumption correlate well with measurements made on in vitro blood samples.

FIG. 1B differs from FIG. 1A in that the percent modulation of the radiation waveform by the pressure waveform is significantly lower than the percent modulation of the pressure waveform itself. Typically, pulse pressure is about 40–50% of diastolic pressure (normal diastolic pressure=80 mm Hg, normal systolic pressure=diastolic pressure+pulse pressure=120 mm Hg), while the transmission peak is typically about 5% of the baseline transmission.

The lower amplitude of the optical modulation is produced by a combination of several factors. Primarily, this decrease in modulation compared to that of the pressure waveform is caused by the fact that the optical phenomena are modulated by the various optical pathlengths in the system, whereas the pressure waveform is transmitted to its sensor with very little loss. Among the factors attenuating the modulation of the optical waveform are the scattering and absorption by the tissue elements in the radiation path, and the additional absorption due to the hemoglobin in the venous blood volume of the tissue, which is not modulated by the cardiac pressure waveform.

Because the optical waveform is only weakly coupled to the pressure waveform, the signal available from the normal arterial pulse is ill-suited for non-invasive measurement of analytes in arterial blood other than the hemoglobin species, which are the dominant absorbing constituents in the blood's absorption spectrum between 700 and 1200 nm. In order to increase the amplitude of the optical pulse and thereby better quantify the concentration of the less absorbing arterial blood constituents, it is desirable to increase the magnitude of the arterial pulse.

In the non-invasive measurement of arterial blood pressure, it is well known that increasing the external pressure on a body part increases the pulse amplitude in the arterial blood pressure waveform. The arterial pressure waveform reaches a maximum when the external pressure is halfway between the resting diastolic (minimum) and systolic (maximum) blood pressure. This phenomenon, which has been explained (Drzewiecki, G. et al., *Annals of Biomedical Engineering*, 22, 89–96 (1994)) based on the change in wall stress in the artery produced by the external pressure, has been employed in commercial devices such as the Finapres (Ohmeda, Englewood, Colo.) and Dinamap (Johnson & Johnson, New Brunswick, N.J.) for non-invasive blood pressure measurement, according to the method first described by Peñaz (Proc. $10^{th}$ Intl. Conf. Med. Biol. Eng., 104, 1973). However, this phenomenon has not been recognized as having useful applications in the non-invasive measurement of arterial blood constituents.

Figure 2:
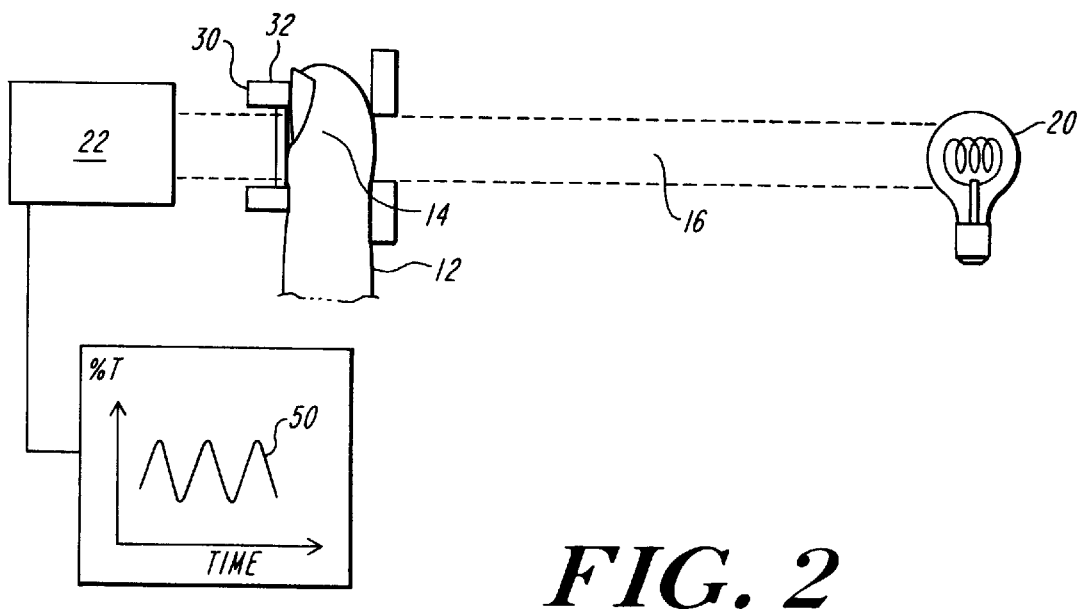
FIG. 2 illustrates an embodiment for practicing the invention by optimizing the magnitude of the arterial pulse by applying a constant mechanical pressure.

Thus, in a first embodiment of the invention, shown in FIG. 2, a controllable pressurization device 10 exerts a specified pressure (exerted by presser 30 and measured, if necessary, by sensor 32) upon a body part 12 located proximate to or within the portion of the optical measurement path 16 between the radiation source 20 and detectors 22 lying within the tissue 14. The pressurization device includes at least one component which may be located in contact with and transmitting the pressure to the measurement site. This component is transparent to the radiation wavelengths intended to interact with the measurement site so that radiation can be transmitted through it. In other, related embodiments, the pressurization device 10 is to be used near, rather than at, the measurement site. In this embodiment, pressurization device 10 need not have a transparent portion.

The optimum level of pressure to be exerted by the pressurization device 10 (the mean arterial pressure) can be determined at the tissue measurement site 14 by examining the optical waveforms 50 produced by the detectors 22 and choosing that pressure which maximizes the coupling between the arterial pressure waveform and the optical waveform. This allows the optimum pressure to be determined on an individual basis and also allows for temporal variations in systolic and/or diastolic blood pressure in an individual.

This configuration permits the use of any type of spectral or temporal distribution of the radiation entering the tissue from the source 20 or leaving the measurement site 14 through the optical path 16 and reaching the detectors 22. Furthermore, this configuration does not restrict the nature or geometry of the optical path, except to require optically transparent components as necessary to carry the radiation into or out of the tissue.

In a preferred embodiment, however, the radiation is broadband and is detected using a plurality of detectors having overlapping frequency responses, as previously disclosed in Block U.S. Pat. No. 5,321,265. In a particularly preferred embodiment, the body part 12 is the last joint of a finger oriented with the finger nail facing away from the radiation source. Since the finger nail serves as a relatively rigid restriction to the propagation of the force created by the cardiac pressure pulse, the application of external pressure to this particular body part when oriented in the manner described can advantageously be unilateral.

In a second embodiment of the invention, the pressurization device 10 exerts a pressure in excess of the subject's natural systolic pressure on the appropriate body part 12 thereby stopping all blood flow through the pressurized region. Such a pressure may be maintained for several seconds at most locations without causing injury. During application of said pressure, the blood in the arteries distal to the site of the application of said pressure continues to flow throughout he capillaries and into the veins, where it is halted from returning to the heart by the applied pressure. The resulting redistribution of blood from the arteries to the veins creates an increase in optical transmission.

When the mechanical pressure is removed, blood immediately re-enters the area previously cut-off, at a flow rate higher than normal. This well-known phenomenon of reactive hyperemia is largely controlled by the autonomic nervous system and has as its purpose the removal of accumulated metabolic wastes from the region and the restoration of normal constituent concentrations in surrounding tissues. This blood inrush increases the blood volume at the measurement site, and cause a sharp decrease in optical transmission through the measurement site. With proper allowance for the changes in the various absorbing species induced by the metabolic changes in the region, these large changes in optical pathlength can be accounted for in the measurements. Furthermore, the large changes in blood volume induced by this method of applying pressure to the body part will also produce large changes in the optical scattering properties of the body part within the optical path. Note that the artificial pulse induced by the sudden release of applied pressure is generally several times larger than the normal cardiac pulse. The detrimental effect of these large changes in optical scattering properties can be reduced by the use, in this embodiment, of detectors having overlapping frequency responses as first disclosed in US Patent 5,321,565. The overlapping spectral sensitivities of the detectors used substantially minimize the effects of changes in the scattering coefficients of the tissue on the modulated signals. This permits the use of a larger blood bolus which in turn provides higher signal-to-background ratios in non-invasive measurements of blood constituent concentrations.

Other methods utilizing applied mechanical pressure are also capable of producing large modulations in the volume of blood, and are therefore useful in this embodiment of the invention. In a preferred example of such a method, a large, pulsatile modulation is achieved by the cyclic elevation and depression of a body part 12 relative to the level of the heart. For ease of mechanical manipulation, the preferred body part is part of a body extremity. Elevation and depression of the body extremity relative to the level of the heart alternately drains and fills the venous blood vessels therein. The change in blood volume caused by such draining and filling causes large changes in the absolute transmission of radiation through the body part 12, and does so without the application of pressure thereon. By avoiding the application of pressure on the body part, this method avoids pressure induced changes in the scattering coefficient of the tissue 14 therein.

In another embodiment of this invention, the modulation required for increased sensitivity may be applied to the tissue itself. In this embodiment, the pressurization 10 applies a periodic pressure to a tissue site in such a manner as to cause deformation of the tissue either by the cyclic movement of extracellular or intracellular fluid into and out of the radiation path within the tissue or by the movement of tissue cellular components into or out of the radiation path. If the applied pressure causes fluid motion, then the required pulse modulated changes in an optical characteristic arise from changes in radiation absorption within the optical path 16. However, if the applied pressure produces movement of tissue cellular components, these movements are more likely to cause changes in scattering characteristics within the optical path. Unlike the previously discussed embodiments, which either employ a constant pressure or employ a variable pressure which exceeds the systolic arterial pressure, in this embodiment of the invention, the applied pressure does not exceed the systolic arterial pressure. In order to create movement of fluids or tissue components within the tissue, the pressurization device 10 applies direct pressure on the measurement site 14. Accordingly, in this embodiment, the pressurization device 10 includes a component transparent to the optical radiation, as disclosed above.

The cyclic movement of fluids or cellular components into and out of the optical path 16 will in turn produce a waveform in the radiation reaching the optical detectors 22. If the optical path within the tissue includes arterial vessels, then this waveform will be superimposed on the optical variations produced by the arterial waveform. However, if there are no arterial vessels within the optical path, then the optical waveform produced by the applied pressure waveform will be the only waveform present. When this is the case, methods well known in the art can provide substantial improvement in signal processing capabilities. The case in which no arteries are in the optical path, is likely to occur when the detectors 22 measure radiation reflected from the tissue measurement site 14. It is well known that under these circumstances, the entering radiation, especially at longer wavelengths (above 1000 nm), does not penetrate the tissue deeply enough to interact with the arterial vessels. Therefore, this embodiment of the invention is particularly useful when the use of longer wavelengths of radiation for the measurements of constituents is desirable.

In some situations, measurements of tissue scattering properties may be required to generate data for correcting the raw measurements made using the methods of this invention. Therefore, in another embodiment of the invention, the pressurization device 10 is modified by the addition of a displacement sensor 34 which allows tissue deformation to be controllably changed by the alteration of pressure applied by the presser 30. In this configuration, the pressurization device 10 can produce and the sensor 34 can measure changes in tissue thickness that are small compared to the total thickness of the tissue within the optical path 16. Because of the high compressibility of most tissues, the pressure required for such small changes is small compared to the pressure required to produce changes in the natural arterial pulse waveform. However, these small pressure variations can change the magnitude and baseline value of the measured optical waveform. It has been discovered that this change is produced almost entirely by changes in the optical pathlength through those components of tissue that are free of arterial blood. These changes in optical pathlength are produced by the reduction in the pathlength through the scattering components of the tissue and by the reduction in the quantity of venous blood remaining in the optical path. By measuring the optical waveform over a range of low applied pressures, it is possible to derive quantitative information regarding the amount of venous blood and the pathlength changes produced by the scattering elements within the tissue. This quantitative information can then be used, along with the other techniques disclosed in this invention, to produce more precise and accurate information about blood and tissue constituent concentrations.

Having described the invention and several embodiments thereof, what is new and secured by Letters Patent is:

1. A method for enhancing the signal-to-background ratio of a non-invasive measurement of the concentration of a blood constituent at a measurement site, the method comprising the steps of:

applying a pressure at a location proximate to a measurement site to stop all of the flow of blood to the measurement site, releasing said pressure to provide a rapid increase of the localized blood volume in the measurement site during a selected interval, illuminating the measurement site with input radiation during at least of a portion of said selected interval, and detecting output radiation representative of the interaction of the input radiation with the blood constituent in the blood at said measurement site during a measurement interval determined by the selected interval.

2. The method of claim 1 wherein the step of increasing the localized blood volume includes the steps of:

releasing the blood rapidly from said area of applied pressure proximate to said measurement site, thereby allowing a blood bolus to flow into the measurement site, thereby transiently increasing the localized blood volume in the measurement site.

3. The method of claim 2 wherein the step of applying pressure comprises applying a mechanical pressure in excess of the natural systolic pressure, and the step of releasing the blood bolus includes the step of reducing the mechanical pressure to below the natural systolic pressure, thereby allowing the blood bolus to enter the measurement site.

4. The method of claim 1 further comprising the step of selecting the measurement site to be the volume distal to the last joint on a finger.

5. The method of claim 1 further comprising the step of selecting a measurement site having a rigid restriction to the force exerted by the cardiac pulse.

6. The method of claim 5 further comprising the step of selecting the rigid restriction to be a fingernail.

7. The method of claim 1 wherein the step of illuminating the measurement site includes the step of selecting a range of illumination wavelengths which includes an absorption wavelength of hemoglobin.

8. The method of claim 7 further comprising the step of selecting the range of illumination wavelengths to extend between 700 and 1200 nanometers.

9. The method of claim 1 wherein the step of detecting the output radiation includes the step of providing a plurality of detectors having overlapping frequency responses.

10. A method for enhancing the signal-to-background ratio of a non-invasive measurement of the concentration of a blood constituent at a measurement site, the method comprising the steps of:

applying, to a location proximate to the measurement site, an external mechanical pressure between the natural systolic pressure and the natural diastolic pressure, illuminating the measurement site with input radiation, and detecting output radiation representative of the interaction of the input radiation with the blood constituent in the blood at the measurement site.

11. The method of claim 10 further comprising the step of selecting the external mechanical pressure to be the average of the natural systolic pressure and the natural diastolic pressure.

12. The method of claim 10 further comprising the step of adaptively selecting the external mechanical pressure to maximize coupling between the output radiation and the arterial blood flow into the measurement site.

13. The method of claim 10 further comprising the step of selecting the measurement site to be a volume distal to the last joint on a finger.

14. The method of claim 10 further comprising the step of selecting a measurement site having a rigid restriction to the force exerted by the cardiac pulse.

15. The method of claim 14 further comprising the step of choosing the rigid restriction to be a fingernail.

16. The method of claim 10 wherein the step of illuminating the measurement site includes the step of selecting a range of illumination wavelengths which includes an absorption wavelength of hemoglobin.

17. The method of claim 16 further comprising the step of selecting the range of illumination wavelengths to extend between 700 and 1200 nanometers.

18. The method of claim 10 wherein the step of detecting the output radiation includes the step of providing a plurality of detectors having overlapping frequency responses.

* * * * *